United States Patent [19]

Senkan

[11] Patent Number: 4,714,796

[45] Date of Patent: Dec. 22, 1987

[54] PRODUCTION OF HIGHER MOLECULAR WEIGHT HYDROCARBONS FROM METHANE

[75] Inventor: Selim M. Senkan, Chicago, Ill.

[73] Assignee: Illinois Institute of Technology, Chicago, Ill.

[21] Appl. No.: 40,853

[22] Filed: Apr. 21, 1987

[51] Int. Cl.$^4$ .................................................. C07C 1/00
[52] U.S. Cl. .................................... 585/328; 585/500; 585/641; 585/943
[58] Field of Search ................ 585/328, 500, 641, 943

[56] References Cited

U.S. PATENT DOCUMENTS

| | | | |
|---|---|---|---|
| 2,320,274 | 5/1943 | Gorin | 260/673 |
| 2,488,083 | 11/1949 | Gorin et al. | 260/677 |
| 2,649,485 | 8/1953 | Taylor et al. | 585/641 |
| 4,199,533 | 4/1980 | Benson | 585/500 |
| 4,301,137 | 11/1981 | Williams et al. | 423/481 |

FOREIGN PATENT DOCUMENTS

| | | |
|---|---|---|
| 1350727 | 4/1974 | United Kingdom . |
| 1443989 | 7/1976 | United Kingdom . |
| 1503239 | 3/1978 | United Kingdom . |

OTHER PUBLICATIONS

Back, M. H. and Back, R. A., "Thermal Decomposition and Reactions of Methane", *Pyrolysis: Theory and Industrial Practice*, Albright, L. F., Crynes, B. L. and Corcoran, W. H., Eds., Academic Press, New York, N.Y., p. 1 (1983).

Weissman, M., and Benson, S., "Pyrolysis of Methyl Chloride, a Pathway in the Chlorine-Catalyzed Polymerization of Methane", *Int. J. Chem. Kinetics*, vol. 16, p. 307 (1984).

Senkan, S. M., Robinson, J. M., and Gupta, A. K., "Sooting Limits of Chlorinated Hydrocarbon-Methane-Air Premixed Flames", *Combust. Flame*, vol. 49, p. 305 (1983).

Frenklach, M., Hsu, J. P., Miller, D. L., and Matula, R. A., "Shock-Tube Pyrolysis of Chlorinated Hydrocarbons: Formation of Soot", *Combust. Flame*, vol. 64, p. 141 (1986).

*Primary Examiner*—Curtis R. Davis
*Attorney, Agent, or Firm*—Thomas W. Speckman; Ann W. Speckman

[57] ABSTRACT

A process for oxidative pyrolysis of halogenated methanes in the presence of oxygen-containing gas under non-flame conditions is provided whereby the formation of solid carbonaceous materials is significantly reduced, while high yields of desired higher molecular weight hydrocarbons such as acetylene and ethylene are maintained.

31 Claims, 1 Drawing Figure

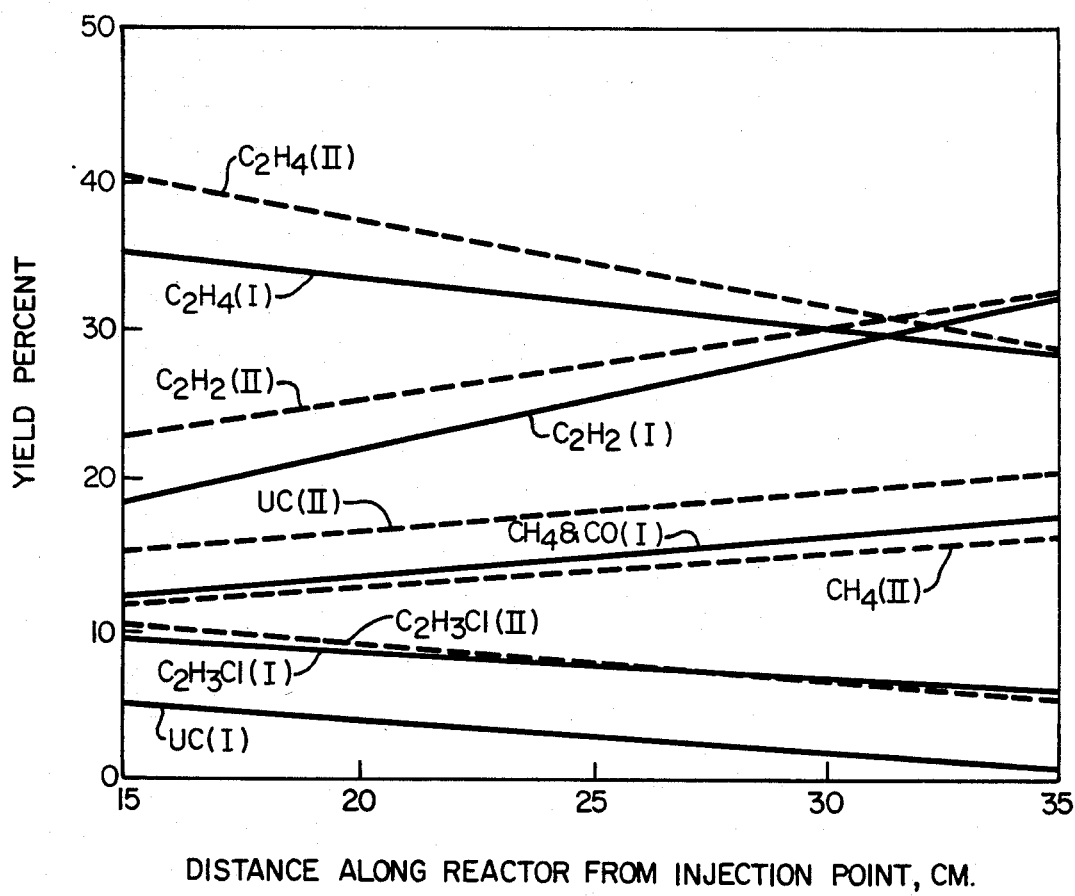

PRODUCTION OF HIGHER MOLECULAR WEIGHT HYDROCARBONS FROM METHANE

This invention was made in part as a result of work under Grant No. R812544-01-1 awarded by the United States Environmental Protection Agency.

BACKGROUND OF THE INVENTION

1. Field of the Invention

This invention relates to gas-phase halogen-catalyzed oxidative-pyrolytic, non-flame, conversion of methane to higher molecular weight hydrocarbons such as acetylene and ethylene. The process of this invention avoids troublesome formation of solid carbonaceous products experienced in prior processes without adversely affecting the yields of higher molecular weight hydrocarbon products. The process of this invention may utilize natural gas as a chemical feedstock in the production of higher molecular weight hydrocarbons, particularly acetylene and ethylene.

2. Description of the Prior Art

Natural gas contains varying quantities of methane, typically about 75 weight percent, and thus constitutes an important raw material for the synthesis of higher molecular weight hydrocarbons. Various processes are known for the conversion of methane into acetylene, ethylene and hydrogen using higher temperature pyrolysis. However, at the high temperatures required for thermal decomposition of methane, the yields of desired higher molecular weight hydrocarbons are reduced due to the formation of excessive amounts of solid carbonaceous products. For example, see Back, M. H. and Back, R. A., "Thermal Decomposition and Reactions of Methane", *Pyrolysis: Theory and Industrial Practice*, Albright, L. F., Crynes, B. L., and Corcoran, W. H., Eds., Academic Press, New York, N.Y., pg. 1 (1983).

U.S. Pat. No. 2,320,274 by Gorin teaches a two step process wherein methane is first converted to methyl halide followed by pyrolysis of methyl halide at about 500° to 1000° C. to form benzene, acetylene, ethylene and hydrogen halide, with benzene being the desired product. Recycle of halogen from the product hydrogen halide also is recognized by this patent. This patent also teaches that large amounts of tar and carbon form as a result of pyrolysis of methyl halides. The U.S. Pat. No. 2,320,274 teaches that oxygen may be used in the oxychlorination of methane to form methyl chloride and water, however, neither oxygen nor water are present in the pryolysis of the methyl halide. U.S. Pat. No. 2,488,083, also by Gorin, teaches a heterogeneously catalyzed process for pryolysis of alkyl halides at temperatures under 500° C. to form hydrocarbons having two or more carbon atoms per molecule. The process of this patent also results in high yield percentages of carbon.

U.S. Pat. No. 4,199,533 by Benson teaches a one step process for conversion of methane to higher molecular weight hydrocarbons by mixing chlorine and methane followed by ignition producing flame temperatures of about 1530° C. producing higher hydrocarbons. The U.S. Pat. No. 4,199,533 teaches that oxygen is not needed, but a small amount can be tolerated so that there is no need to purge the reactor prior to use. It should be recognized that under steady state operating conditions, no oxygen would be present according to the teachings of the Benson U.S. Pat. No. 4,199,533. Weissman and Benson studied the kinetics of high temperature pyrolysis of methyl chloride under non-flame conditons. Weissman, M., and Benson, S., "Pyrolysis of Methyl Chloride, a Pathway in the Chlorine-Catalyzed Polymerization of Methane", *Int. J. Chem. Kinetics.*, v.16, p.307 (1984). The Weissman and Benson publication also describes the formation of significant amounts of carbon. Papers by Senkan et al and Frenklach et al also point out the importance of soot or carbon formation during combustion and pyrolysis of chlorinated methanes. Senkan, S. M., Robinson, J. M., and Grupta, A. K., "Sooting Limits of Chlorinated Hydrocarbon-Methane-Air Premixed Flames", *Combust. Flame*, v. 49, p. 305 (1983). Frenklach, M., Hsu, J. P., Miller, D. L., and Matula, R. A., "Shock-Tube Pyrolysis of Chlorinated Hydrocarbons", *Combust. Flame*, v.64, p.141 (1986).

The prior art has, in summary, recognized the practical and commercial significance of production of higher molecular weight hydrocarbons from methane, but has also recognized the limitations imposed by the formation of carbonaceous deposits such as tars, solid carbon and soot.

SUMMARY OF THE INVENTION

This invention provides a process for oxidative pyrolysis of halogenated methanes in the gas phase and under non-flame conditions in the presence of oxygen which significantly reduces the formation of carbonaceous deposits, such as tars, solid carbon and soot, while maintaining high yields, in the order of 20 to 80 percent, of desired higher molecular weight hydrocarbon products. According to a preferred embodiment, the process of this invention may be a two step process wherein the first step involves the halogenation of methane using any of the well known methods of the art. These methods include direct halogenation of methane using a halogen containing gas or oxyhalogenation using hydrogen halide in the presence of oxygen. Then in a second step, the halogenated methanes are oxidatively pyrolyzed under non-flame conditions in the presence of an oxygen containing gas. The process of this invention may also be a single step process wherein the methane halogenation and the oxidative pyrolysis of halogenated methanes are accomplished in a single vessel. According to this invention, oxygen converts to carbon monoxide hydrocarbon compounds which would otherwise result in the formation of carbonaceous deposits during conversion of halogenated methanes. Oxidative pyrolysis of the halogenated methanes yields higher molecular weight hydrocarbons such as acetylene and ethylene.

BRIEF DESCRIPTION OF THE DRAWING

Further features of the invention will be apparent from the following detailed description of the invention and the examples, read in conjunction with the drawing, wherein:

The drawing shows the yield percentages of indicated materials as a function of the distance along a reactor from injection point for oxidative pyrolysis of monochloromethane and pyrolysis of monochloromethane in absence of oxygen, as described in Examples I and II, respectively.

DESCRIPTION OF PREFERRED EMBODIMENTS

The process of the present invention provides oxidative pyrolysis of halogenated methanes in the presence of an oxygen containing gas to provide high yields, in the order of 20 to 80 percent, of higher molecular weight hydrocarbon products and to prevent the formation of carbonaceous deposits.

A preferred embodiment may comprise a one or two step process wherein a feedstock gas comprising methane is first converted into halogenated methanes, and oxidative pyrolysis of halogenated methanes is then carried out in the gas phase and under non-flame conditions.

The halogenated methanes used in the oxidative pyrolysis of this invention may include, mono-, di-, tri-, and tetra-halogenated methanes. Halogenated methanes may be produced by any suitable method known to the art, such as those referred to in U.S. Pat. Nos. 2,320,274, 2,488,083 and 4,199,533. The halogenation of methane may be carried out in the same reaction vessel or in a reaction vessel separate from the oxidative pyrolysis of this invention.

The oxidative pyrolysis of halogenated methanes according to this invention is carried out at temperatures of about 500° C. to about 1500° C., preferably about 900° C. to about 1200° C., and under pressures of about 0.5 atmosphere to about 50 atmospheres, preferably about 1 atmosphere to about 5 atmospheres. Suitable reaction chambers capable of withstanding the temperature and pressure requirements of the present invention are well known to the art.

Feedstock gas comprising methane suitable for use in the process of this invention may comprise any methane containing gas which does not contain interfering compounds. Preferably, the methane containing gas suitable for use as a feedstock in the process of this invention comprises at least about 25 percent by weight methane and may comprise up to 100 percent by weight methane. Sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other gases such as ethane, propane, acetylene and ethylene, which produce corresponding chemical reactions to those of methane in the process of this invention. Purification of such mixed gases comprising principally methane is not usually necessary. These sources of methane containing gas and processes for producing methane are well known in the art.

Any source of halogen containing gas which does not contain interfering chemical compounds may be used in the process of this invention. It is preferred that the halogen containing gas contain at least about 25 percent and may contain up to 100 percent by weight halogen selected from the group consisting of chlorine, bromine, iodine, and mixtures thereof. Chlorine is a preferred halogen for use in this invention. Halogen containing gas may be largely supplied by recycle of gas obtained by recovery of the halogen acid which forms in the oxidative pyrolysis process. Such halogen recovery may be by any method known to the art, such as taught by U.S. Pat. Nos. 2,320,274 and 4,199,533. Make-up halogen may be added as required. According to the process of this invention, the gaseous mixture comprising halogenated methanes and oxygen is fed to the oxidative pyrolysis reaction zone in the halogenated methanes/oxygen mole percentage ratios of about 1 to about 100, preferably about 5 to about 20.

Any oxygen containing gas which does not contain interfering chemical compounds and can provide the above specified halogenated methanes/oxygen mole percentage ratios in the particular reaction system are suitable for use in the process of this invention. Also, any oxygen containing precursor compound, such as steam, which under conditions of this process provides oxygen, may be suitable for use in this invention. The term "oxygen containing gas" as used throughout this disclosure and claims refers to gas containing oxygen, such as air or steam, and gases having an oxygen content of up to 100 percent. It is preferred to use oxygen containing gas comprising over about 50 volume percent oxygen.

It is a further requirement of the oxidative pyrolysis process of this invention that the reaction be carried out under non-flame conditions. These non-flame conditions are maintained by selection of temperature, pressure and specific gas ratios which do not lead to flame formation. These conditions can be ascertained by one skilled in the art in view of the above parameters. Utilization of broad operating conditions, as set forth above, is rendered possible due to the known flame inhibiting characteristic of halogens and halogenated compounds. Carrier gases or mixtures may be used to reduce the concentration of active reactants. Inert carrier gas may be used, or other gases which do not contain interfering compounds may be used. Methane or any gaseous source of methane may be used as a carrier gas.

The following specific examples compare the results and products of oxidative pyrolysis of monochloromethane according to a preferred embodiment of the process of the present invention to pyrolysis of monochloromethane in the absence of oxygen. These examples use methyl chloride obtained by chlorination of methane in a first step by any suitable process. The specific examples are intended to be illustrative only and are not intended to limit the present invention in any way.

EXAMPLE I

Oxidative pyrolysis of monochloromethane was carried out at a pressure of about 0.7 atmosphere in a transparent quartz reactor 100 cm long and having an inner diameter of 2.1 cm placed in a three zone electric tube furnace. Argon carrier gas was preheated in the first zone of the furnace, extending about 15 cm, to a temperature of about 980° C. Monochloromethane was mixed with oxygen and the mixture injected into the preheated argon carrier gas to rapidly heat the mixture of monochloromethane and oxygen to reaction temperature of 980° C. The resulting mixture composition was 7.32 mole percent monochloromethane, 2.05 mole percent oxygen, and the balance argon carrier gas. The reactant gas mixture of monochloromethane and oxygen in the argon carrier gas was passed through the reaction zone at a velocity sufficient to result in a mean reaction time in the range of 50 to 250 milliseconds.

Gas samples were withdrawn through a cooled quartz sampling probe positioned centrally at points along the length of the reactor. The withdrawn gases were analyzed by a mass spectrometer. Major species quantified were $C_2H_2$, $C_2H_4$, $C_2H_6$, $C_2H_3Cl$, $CH_3Cl$, $O_2$, Ar, $CH_4$, HCl and CO. Only trace levels of $CO_2$ and $H_2O$ were measured.

The transparent quartz reactor was operated under the above conditions for up to 4 to 5 hours without any visible signs of formation of carbonaceous deposits at the reactor exit.

The solid lines in the drawing show the yield percent of product gases, including $C_2H_2$, $C_2H_4$, $C_2H_3Cl$, $CH_4$ and CO calculated from the mole percent of product gases quantified along the reactor length during oxidative pyrolysis of monochloromethane as described above. The drawing also shows, in solid lines, the yield percent of unaccounted carbon (UC) representing the carbon converted but not accounted for in the measurements of $C_2H_2$, $C_2H_4$, $C_2H_3Cl$ and CO.

EXAMPLE II
(COMPARATIVE)

The same reaction system was operated and analyzed in the fashion described above, at a pressure of about 0.7 atm and a temperature about 980° C., except that pyrolysis of monochloromethane was conducted in the absence of oxygen. Monochloromethane was injected into a preheated carrier gas resulting in a mixture of 7.47 mole percent monochloromethane and the balance argon carrier gas.

In the pyrolysis of monochloromethane in the absence of oxygen, black solid deposits were immediately formed on the interior of the transparent quartz reactor, rendering it opaque. The tip of the cooled sampling probe was also coated with carbonaceous deposits.

The dashed lines in the drawing show the yield percent of product gases, including $C_2H_2$, $C_2H_4$, $C_2H_3Cl$ and $CH_4$ calculated from the mole percent of product gases quantified along the reactor length during pyrolysis of monochloromethane in the absence of oxygen as described above. As should be noted, hydrocarbon product yields of $C_2H_2$ and $C_2H_4$ were similar to those obtained in Example I shown by solid lines. The drawing illustrates that unaccounted carbon (UC), which is related to the formation of carbonaceous solids, is significantly higher in Example II than Example I in which oxygen was present.

As seen in the drawing, carbon monoxide forms during oxidative pyrolysis of monochloromethane in Example I, and its formation was in the same order as the reduction in unaccounted carbon (UC) yields between Examples I and II. Since carbon monoxide is a gaseous product, it can be handled more easily than carbonaceous deposits and can itself be utilized in the production of higher molecular weight hydrocarbons.

As shown in the drawing, ethylene and acetylene are the principal higher molecular weight hydrocarbon products, and their production is not inhibited or reduced in the presence of an oxygen containing reactant gas according to the process of this invention. The drawing also illustrates the significant reduction in production of carbon as unaccounted carbon in the oxidative pyrolysis process according to this invention compared to pyrolysis of monochloromethane in the absence of oxygen. Therefore, the presence of oxygen in the pyrolysis of halogenated methanes according to the process of the present invention reduces the formation of carbonaceous deposits without reducing the yields of desired higher molecular weight hydrocarbons, such as acetylene and ethylene.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. A process for producing higher molecular weight hydrocarbons from a gas comprising halogenated methanes, said process comprising:
    oxidatively pyrolyzing said halogenated methanes under non-flame conditions in the presence of an oxygen-containing gas.

2. A process for producing higher molecular weight hydrocarbons as described in claim 1 wherein temperatures are maintained at about 500° C. to about 1500° C.

3. A process for producing higher molecular weight hydrocarbons as described in claim 1 wherein temperatures are maintained at about 900° C. to about 1200° C.

4. A process for producing higher molecular weight hydrocarbons as described in claim 1 wherein pressures are maintained at about 0.5 atmosphere to about 50 atmospheres.

5. A process for producing higher molecular weight hydrocarbons as described in claim 1 wherein pressures are maintained at about 1 atmosphere to about 5 atmospheres.

6. A process for producing higher molecular weight hydrocarbons as described in claim 1 wherein the mole percentage ratio of halogenated methanes to oxygen is about 1 to about 100.

7. A process for producing higher molecular weight hydrocarbons as described in claim 1 wherein the mole percentage ratio of halogenated methanes to oxygen is about 5 to about 20.

8. A process for producing higher molecular weight hydrocarbons described in claim 1 wherein temperatures are maintained at about 500° C. to about 1500° C., pressures are maintained at about 0.5 atmosphere to about 50 atmospheres, and the mole percentage ratio of halogenated methanes to oxygen is about 1 to about 100.

9. A process for producing higher molecular weight hydrocarbons as described in claim 1 wherein said halogenated methanes principally comprise monochloromethane.

10. A process for producing higher molecular weight hydrocarbons as described in claim 1 wherein said oxygen-containing gas comprises over about 50 volume percent oxygen.

11. A process for producing higher molecular weight hydrocarbons as described in claim 1 wherein said oxygen-containing gas comprises steam.

12. A process for producing higher molecular weight hydrocarbons as described in claim 1 wherein said higher molecular weight hydrocarbons yield comprises acetylene and ethylene in combined yield percentage of about 20 to about 80 percent.

13. A process for producing higher molecular weight hydrocarbon as described in claim 1 wherein temperatures are maintained at about 500° C. to about 1500° C., pressures are maintained at about 0.5 atmosphere to about 50 atmospheres, the mole percentage ratio of halogenated methanes to oxygen is about 1 to about 20, said halogenated methanes principally comprise monochloromethane, and said higher molecular weight hydrocarbons yield comprises acetylene and ethylene in combined yield percentage of about 20 to about 80 percent.

14. A process for producing higher molecular weight hydrocarbons from a gas comprising methane, said process comprising: halogenating said methane by a process of reacting said methane with a reactant selected from the group consisting of halogen containing gas and hydrogen halide, said hydrogen halide in the presence of oxygen, to form halogenated methanes and oxidatively pyrolyzing said halogentated methanes under non-flame conditions in the presence of an oxygen-contaning gas.

15. A process for producing higher molecular weight hydrocarbons from a gas comprising methane as described in claim 14 wherein the halogenated methanes to oxygen mole percentage ratio is about 1 to about 100.

16. A process for producing higher molecular weight hydrocarbons from a gas comprising methane as described in claim 14 wherein the halogenated methanes to oxygen mole ratio is about 5 to about 20.

17. A process for producing higher molecular weight hydrocarbons from a gas comprising methane as described in claim 15 wherein said oxidatively pyrolyzing said halogentated methanes is carried out at temperatures about 500° C. to about 1500° C. and pressures about 0.5 atmosphere to about 50 atmospheres.

18. A process for producing higher molecular weight hydrocarbons from a gas comprising methane as described in claim 17 wherein said halogenated methanes principally comprise monochloromethane, and said higher molecular weight hydrocarbons yield comprises acetylene and ethylene in combined yield percentage of about 20 to about 80 percent.

19. In a process for producing higher molecular weight hydrocarbons from a gas comprising methane wherein said methane is converted to halogenated methanes, the improvement comprising: oxidatively pyrolyzing said halogenated methanes under non-flame conditions in the presence of an oxygen-containing gas.

20. In a process according to claim 19 wherein temperatures are maintained at about 500° C. to about 1500° C.

21. In a process according to claim 19 wherein temperatures are maintained at about 900° C. to about 1200° C.

22. In a process according to claim 19 wherein pressures are maintained at about 0.5 atmosphere to about 50 atmospheres.

23. In a process according to claim 19 wherein pressures are maintained at about 1 atmosphere to about 5 atmospheres.

24. In a process according to claim 19 wherein the mole percentage ratio of halogenated methanes to oxygen is about 1 to about 100.

25. In a process according to claim 19 wherein the mole centage ratio of halogenated methanes to oxygen is about 5 to about 20.

26. In a process according to claim 19 wherein temperatures are maintained at about 500° C. to about 1500° C., pressures are maintained at about 0.5 atmosphere to about 50 atmospheres, and the mole percentage ratio of halogenated methanes to oxygen is about 1 to about 100.

27. In a process according to claim 19 wherein said halogenated methanes principally comprise monochloromethane.

28. In a process according to claim 19 wherein said oxygen-containing gas comprises over about 50 volume percent oxygen.

29. In a process according to claim 19 wherein said oxygen-containing gas comprises steam.

30. In a process according to claim 19 wherein said higher molecular weight hydrocarbons yield comprises acetylene and ethylene in combined yield percentage of about 20 to about 80 percent.

31. In a process according to claim 19 wherein temperatures are maintained at about 500° C. to about 1500° C., pressures are maintained at about 0.5 atmosphere to about 50 atmospheres, the mole percentage ratio of halogenated methanes to oxygen is about 1 to about 100, said halogenated methanes principally comprise monochloromethane, and said higher molecular weight hydrocarbons yield comprises acetylene and ethylene in combined yield percentage of about 20 to about 80 percent.

* * * * *